(12) United States Patent
McInerney et al.

(10) Patent No.: US 6,306,191 B1
(45) Date of Patent: Oct. 23, 2001

(54) SANITARY SEAL DESIGN AND VENT USING SUCH SEAL

(75) Inventors: Kevin G. McInerney, Chelmsford; Joseph M. Almasian, Watertown; Chau Nguyen, Boston, all of MA (US)

(73) Assignee: Millipore Corporation, Bedford, MA (US)

( * ) Notice: Subject to any disclaimer, the term of this patent is extended or adjusted under 35 U.S.C. 154(b) by 0 days.

(21) Appl. No.: 09/438,451

(22) Filed: Nov. 12, 1999

(51) Int. Cl.$^7$ ........................................... B01D 46/00
(52) U.S. Cl. .................... 55/385.4; 55/385.1; 55/502; 210/321.75; 604/333
(58) Field of Search ...................... 55/385.1, 385.4, 55/502, 504, 505; 604/333, 335; 210/321.75, 321.84; 454/339, 340; 285/335

(56) References Cited

U.S. PATENT DOCUMENTS

| | | | | |
|---|---|---|---|---|
| 4,449,970 | * | 5/1984 | Bevan et al. ........................ | 55/385.4 |
| 4,875,899 | * | 10/1989 | Holtermann ......................... | 604/333 |
| 5,372,594 | * | 12/1994 | Colacello et al. .................... | 604/333 |
| 5,609,757 | * | 3/1997 | Schiavo et al. ...................... | 55/502 |
| 5,725,645 | * | 3/1998 | Wickland et al. .................... | 55/385.4 |
| 5,733,271 | * | 3/1998 | Bjorn ................................. | 55/385.4 |
| 5,885,453 | * | 3/1999 | Chatelin et al. ..................... | 55/385.4 |
| 5,891,223 | * | 4/1999 | Shaw et al. .......................... | 55/385.4 |
| 5,914,415 | * | 6/1999 | Tago ................................... | 55/385.1 |
| 6,032,802 | * | 3/2000 | Ejima et al. ......................... | 55/385.4 |

* cited by examiner

Primary Examiner—David A. Simmons
Assistant Examiner—Minh-Chau T. Pham
(74) Attorney, Agent, or Firm—John Dana Hubbard; Timothy J. King; Paul J. Cook

(57) ABSTRACT

A seal, a vent for a filter housing and a system for using them.

The seal is designed a first outer seal having a closed outer periphery that divides and isolates a first inner area from the outside environment and a second inner seal formed along a portion of the inner surface of the first outer seal and forming a second inner area within the first inner area and which is isolated from both the first inner area and the outside environment.

The seal is incorporated into a vent for a filter housing having opening is contained within a vent area and the opening is offset from the center of the vent area. The opening establishes a fluid pathway from the interior to the exterior of the filter device. The inner seal surrounds the vent opening. The outer seal also surrounds the vent opening at one of its ends and surrounds the entire periphery of the vent area so as to isolate the vent area from the area outside of the vent area. A vent cap is secured at its outer periphery to the outer periphery of the vent area. The cap has an exhaust port which when in alignment with the vent allows fluid to flow out of the housing interior. The exhaust port is offset from the center of the cap and is designed to align with the offset opening of the vent. The cap is either moved in a linear or rotational motion and the vent opening and the cap opening are always contained within the area defined by the outer seal so as to form a sanitary seal.

Also disclosed in a sanitary recovery system utilizing the seal and vent of the present invention.

8 Claims, 7 Drawing Sheets

SANITARY SEAL DESIGN AND VENT USING SUCH SEAL

The present invention relates to a sanitary seal and its use in a vent system. More particularly, it relates to a sanitary seal and vent used on filter cartridges.

BACKGROUND OF THE INVENTION

In the processing of liquids through devices such as filters, it is well known that gases are formed within the fluid often within the filter itself. These gases are either gases which had been entrained or dissolved within the fluid and which have now come out as bubbles within the liquid or are introduced into the fluid during processing.

These gases need to be removed in order to have efficient filtration. Gas tends to block portions of the filter surface making them unusable for filtration. When enough gas is formed on the filter surface, the filtration process essentially stops.

Additionally, many manufacturers of these liquids prefer or require that no gas be contained or visible within their finished product. Therefore it is important if not imperative to remove the gas.

Typically, vents are formed on the upstream side of the filter housing so as to allow for the removal of gas from the liquid. The venting must be done in a manner that maintains a sanitary seal between the vent opening and the outside environment when the vent is closed.

These vents are sealed with a push/pull valve design as shown in prior art FIG. 1. A vent stop 10 is mounted within the opening 12 of the vent 14. The stop selectively opens and closes the vent 14 via a series of O-rings 16A and 16B. The vent 14 is opened by pulling the stop 10 outward until a passageway 18A is established with the passageway 18B of the vent opening 12. Gas that is at a higher pressure within the filter housing than the outside atmosphere flows from the inside of the housing to the outside of the housing via the passageways 18A and 18B. The vent 14 is closed by pushing the vent stop 10 back into the vent opening 12 so the passageway 18A is against the inclined portions 20 of the vent opening 12 which prevent any fluid (liquid or gas) from exiting the vent 14.

Such vents are required on many filters because venting must be done on a periodic basis to prevent gases from building up inside the filter such that performance is compromised. Typically, gas build up diminishes the efficiency of filters and the vents must be periodically opened to vent the accumulated gases.

To determine if accumulated gases are affecting performance, one may monitor the pressure drop of the filter (increases by a set % require venting) or throughput (decreases in a set % require venting). One may also dispense with such monitoring and merely schedule periodic filter venting.

A problem with prior art vent designs is that the vents need to be small, but are not ergonomically designed. They have an outer knurled surface designed to be manipulated in a cam fashion that is bruises the hands. Also, the cam action required coupled with the strong hand action needed to actuate the cam can result in de-coupling the vent stop from the vent housing or stripping the cam from the housing.

Another issue is that the prior art design does not allow one to open the vent sufficiently so as to allow the gas to escape in a reasonable amount of time. But, one does not want to open the prior art vent so quickly that the sanitary seal is compromised, such as actually pulling the stop off the vent or more commonly, fluid leaks out of the vent and along the outside of the vent where it is lost (on prior art vents that have only a single o-ring).

What is needed is a new sanitary seal and vent design using that seal which overcomes these problems. The present invention provides such a solution.

SUMMARY OF THE INVENTION

The present invention relates to a seal, a vent for filter housings incorporating said seal and a device for recovering degassed fluids that incorporates the seal and vent.

The present invention provides a seal design having a first outer seal having a closed outer periphery that isolates a first inner area from the outside environment and a second inner seal formed along a portion of the inner surface of the first outer seal and forming a second inner area within the first inner area and which is isolated from both the first inner area and the outside environment.

The seal is incorporated into a vent for a filter housing having an opening contained within a vent area and the opening being offset from the center of the vent area. The opening establishes a fluid pathway from the interior to the exterior of the filter device. The inner seal surrounds the vent opening. The outer seal also surrounds the vent opening at one of its ends and surrounds the entire periphery of the vent area so as to isolate the vent area from the area outside of the vent area. A vent cap is secured to the vent housing such that it is movably fixed to the vent housing and its periphery contacts the outer periphery of the seal such that the vent area is enclosed.

The cap has an exhaust port which when in alignment with the vent allows fluid to flow out of the housing interior. The exhaust port is offset from the center of the cap and is designed to align with the offset opening of the vent. The cap is either moved in a linear or rotational motion and the vent opening and cap opening are always contained within the area defined by the outer seal so as to form a sanitary seal whether the cap is positioned to vent or not.

Also disclosed is a sanitary recovery system utilizing the seal and vent of the present invention.

It is an object of the present invention to provide a first seal having a second seal formed as part of its inner surface.

It is a further object of the present invention to provide a seal having a first outer seal having a closed outer periphery that divides and isolates a first inner area from the outside environment and a second inner seal formed along a portion of the inner surface of the first outer seal and forming a second inner area within the first inner area and which is isolated from both the first inner area and the outside environment.

It is an additional object of the present invention to provide a seal having a first outer seal formed such that its periphery seals a first selected area from an outside environment and a second inner seal formed as part of the inner surface of the outer seal within the first selected area, the periphery of the second seal forming a second selected area which is sealed from both the first selected area and the outside environment.

It is another object of the present invention to provide a vented filter housing comprising a housing, a vent opening contained within a vent area, the opening being offset from the center of the vent area, the opening establishing a fluid pathway from the interior to the exterior of the filter, a seal having an inner seal and an outer seal, the inner seal being formed as part of the inner periphery of the outer seal, the inner seal surrounding the vent opening, the outer seal also surrounding the vent opening and surrounding the entire periphery of the vent area so as to isolate the vent area from the area outside of the vent area and a vent cap secured at its outer periphery to an outer periphery of the vent area, the cap having an opening in its bottom portion in fluid communication with an exhaust port, the cap opening being offset from the center of the bottom of the cap so it can be aligned with the offset opening of the vent to facilitate venting.

It is an object of the present invention to provide a closed loop venting/liquid recovery system that includes the vent of the present invention as well as a channel from the exhaust port to a receptacle positioned to receive the effluent from the exhaust port. It would be preferable, where sterility is desired, for the channel is isolated from the outside environment.

DETAILED DESCRIPTION OF THE INVENTION

The present invention is related to a sanitary seal which is in actuality a seal within a seal, its use in a vent system and its use with that vent system to sanitarily recover vented fluid. Through the use of this seal design, one is able to form a vent that is simple to operate (requiring either a linear motion or rotation to open or close) and which establishes and maintains a sanitary seal and to recover fluid which is vented in a sanitary condition.

Figure 1:
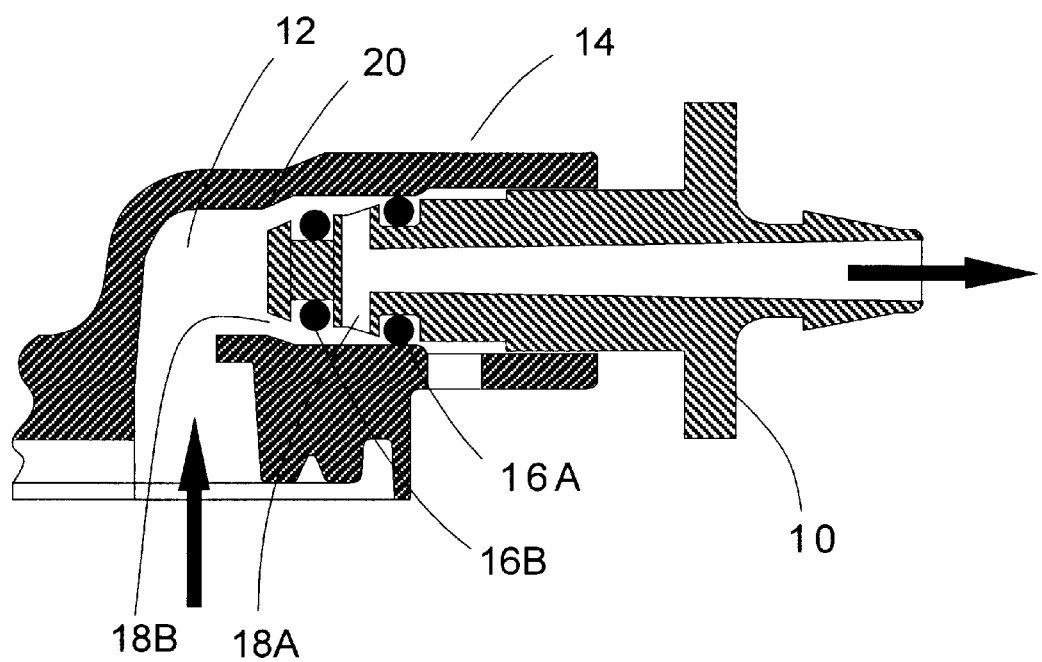
FIG. 1 shows a prior art vent and seal in planar view.
Figure 2:
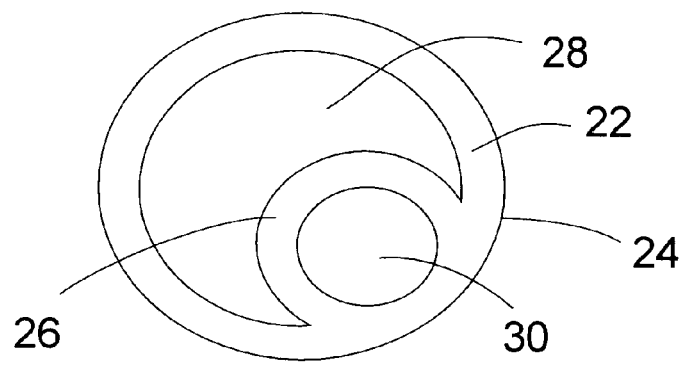
FIG. 2 shows a first embodiment of the seal of the present invention in planar view.
Figure 3:
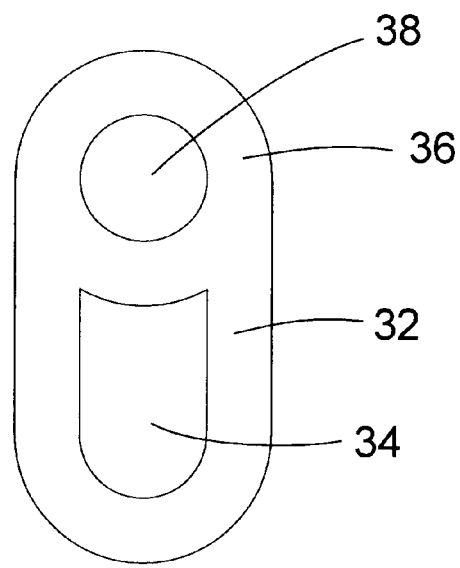
FIG. 3 shows a second embodiment of the seal of the present invention in planar view.

As shown in FIG. 2, the seal design is formed of a first outer seal 22 that has a closed outer periphery 24. As shown, the seal is of a circular design, however as shown in FIG. 3 and as will be appreciated from the teachings of this application it may be of other shapes. A second seal 26 is formed within the first seal 22 and is attached to a part of the inner surface of the first seal 22. In this manner, the first seal 22 forms an area 30 that is isolated from the outside environment by the closed outer periphery 24 of the seal 22. The second seal 26 forms a second isolated area 30 which is contained within the first area 28 and isolated form both it and the outside environment.

FIG. 3 shows another embodiment of the seal. In this instance, outer seal 32 is formed as an ovoid having a closed outer periphery that defines a first closed area 34. The second seal 36 is formed inside the first seal 32 and forms the second area 38 within the second seal 36 that is isolated from the first area 34 and the outside environment.

Figure 4:
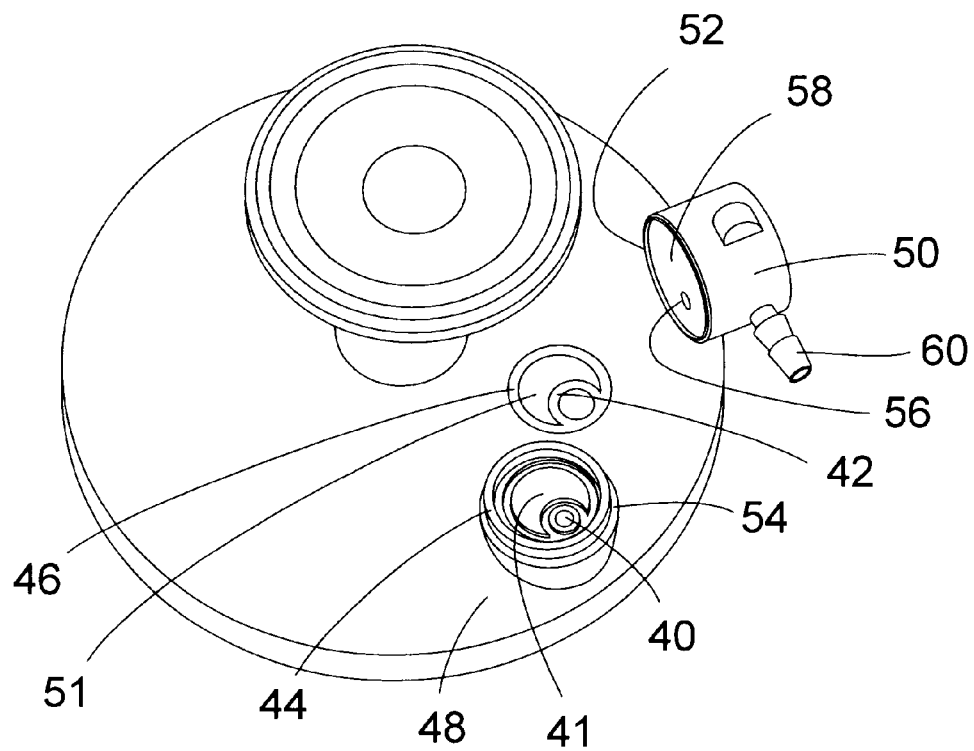
FIG. 4 shows the seal and vent design of the present invention in exploded view.

FIG. 4 shows the seal of FIG. 2 in use on a filter device. As can be seen, the opening 40 is contained within a vent area 41 and the opening 40 is offset from the center of the vent area 41. The opening 40 establishes a fluid pathway from the interior to the exterior of the filter device. The inner seal 42 surrounds the vent opening 40. The outer seal 46 also surrounds the vent opening 40 at one of its ends and surrounds the entire periphery of the vent area 41 so as to isolate the vent area from the area 48 outside of the vent area 41. A vent cap 50 is secured at its outer periphery 52 to the outer periphery 54 of the vent area 41. The cap 50 has an opening 56 in its bottom portion 58 that is in fluid communication with an exhaust port 60 on the side of the cap 50. If desired, this exhaust port could be mounted on the top of the cap 50. Its location is not critical to the invention. The opening 56 is offset from the center of the bottom of the cap 50 and is designed to align with the offset opening 40 of the vent.

When the vent is closed, the opening 56 of the cap is positioned within the sealed vent area 51, which is defined by the periphery of the outer seal 42 and the outer wall of the seal 46. In addition, when the vent is off, the vent opening 40 is surrounded by the inner seal 42 and covered by the closed bottom 58 of the cap 50, such closed bottom having an interference fit with such seal sufficient to block ingress or egress of fluid.

To open the vent, the cap 50 is rotated either in a clockwise or counterclockwise direction (either will work) until the opening 56 in the cap 50 is aligned with the opening 40 in the vent area 41. If desired, one may include a mechanical stop (not shown) or corresponding marks or lugs on the cap 50 and outer surface 48 of the filter device to indicate when the two openings 40, 56 are in alignment. Gas and sometimes some liquid will exit the vent opening 40, enter the cap opening 56 and travel via the channel (not shown) in the cap 50 to the exhaust port 60. As shown in this Figure, the exhaust port 60 is a bayonet type fixture to which a tube (not shown) may be attached. Gas and any liquid can then be shunted as desired to a drain (not shown) or a recovery vessel (as described below).

Figure 5:
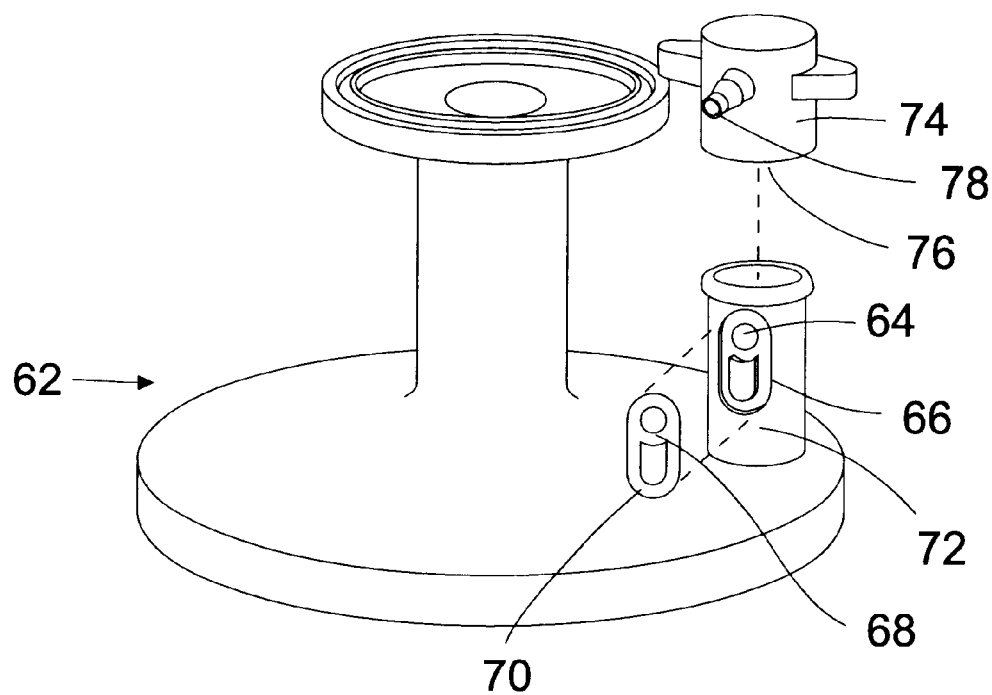
FIG. 5 shows a second embodiment of the seal and vent design of the present invention in an exploded view.

FIG. 5 shows a second vent design according to the present invention. In this embodiment, the vent is opened and closed by a linear motion rather than a rotational motion as used in the embodiment of FIG. 4. The filter device 62 contains a vent opening 64 surrounded by a vent area 66. Again, as with the embodiment of FIG. 4, the vent opening 64 is offset within the vent area 66. The opening 64 establishes a fluid pathway from the interior to the exterior of the filter device 62. The inner seal 68 surrounds the vent opening 64. The outer seal 70 also surrounds the vent opening 64 at one of its ends and surrounds the entire periphery of the vent area 66 so as to isolate the vent area from the area 72 outside of the vent area 66. A vent cap 74 is slidably secured by its inner surface 76 to the outer surface of the vent area 66. The cap 74 has an exhaust port 78 in its side portion that establishes a fluid pathway from the interior to the exterior of the cap 74. The port 78 is designed to align with the offset opening 64 of the vent.

The vent is operated in the following manner. When the vent is off, the port 78 of the cap 74 is located within the sealed area defined by the closed periphery of the outer seal 70. The vent opening 64 is surrounded by the inner seal 68 and covered by the closed, solid sidewall of the cap 74. In this manner, fluid (gas or liquid) is prevented from exiting the vent opening 64. To open the vent, the cap 74 is moved linearly in an upward direction until the vent opening 64 aligns with the port 78 of the cap 74. If desired one may include a mechanical stop (not shown) such as corresponding marks or lugs on the cap 74 and surface of the vent to limit the extent of travel or indicate when the two openings 78 and 64 are in alignment. Gas and sometimes some liquid will exit the vent opening 64 enter the port 78 and travel via the port 78 to the outside. As shown in this Figure, the exhaust port 78 is a bayonet type fixture to which a tube (not shown) may be attached. Gas and any liquid can then be shunted as desired to a drain (not shown) or a recovery vessel (as described below). While this embodiment has been shown with a vertical linear motion, it may also be used in other manners that utilize a linear motion or it may be combined with a slight rotational motion such that the vent is opened and closed as the cap is moved linearly and rotationally relative to the opening. The type of movement and its placement and design are not critical to the invention.

By using the seal and vent design of the present invention one provides a vent and cap opening which are always contained within a sealed area regardless of whether it is in a closed or open position. This provides one several advantages. The vent and its components are always kept in an isolated sanitary condition. This is of particular interest to the pharmaceutical, biopharmaceutical and food and beverage industries. Additionally, by containing the vent within a seal system, any leakage that otherwise would have moved down the length of the vent and/or filter housing is retained within the vent seal and therefore directed to the exhaust port. This eliminates the current problem with leakage of materials which lead to unsanitary conditions and the exposure of workers to hazardous or biological materials.

The housing may be made of a plastic, preferably a thermoplastic including polyolefins such as polyethylenes including ultrahigh molecular weight polyethylenes, polypropylenes; copolymers or terpolymers of polyolefins; nylons; PTFE resin, PFA, PVDF, ECTFE, and other fluorinated resins, particularly perfluorinated thermoplastic resins; polycarbonates; metallocene derived polymers, polysulphones; modified polysulphones such as polyethersulphone, polyarylsulphones or polyphenylsulphones; any glass or other reinforced plastic; or a metal such as stainless steel, aluminum, copper, bronze, brass, nickel, chromium or titanium or alloys or blends thereof.

The seal is preferably made of a rubber, natural or synthetic such as butyl rubber, nitrile rubber or silicone rubber or a plastic such as PTFE resin, other fluorinated resins such as PFA, PVDF, ECTFE, with perflourinated thermoplastic resins being preferred; styrene butadiene rubber, EPDM, carboxylated styrene butadiene rubber, polyisoprene, styrene isoprene styrene copolymers styrene butadiene styrene copolymers, styrene ethylene butylene styrene copolymers, polystyrenes, EVA copolymers, urethanes and other such materials commonly used to form resilient seals.

Figure 6:
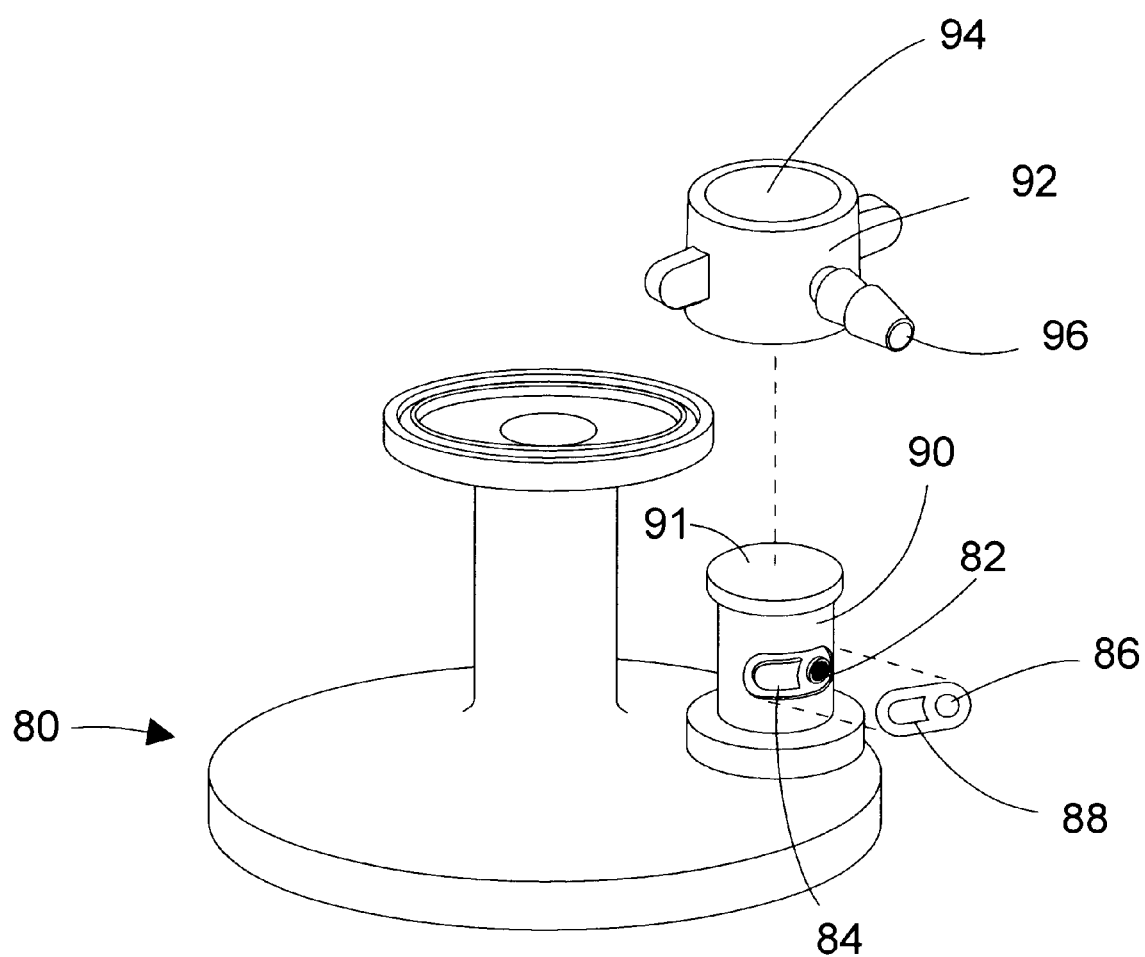
FIG. 6 shows a third embodiment of the seal and vent design of the present invention in an exploded view.

FIG. 6 provides a vent of the present invention similar to FIG. 5, the difference being the cap 92 does not have a solid top, rather the cap 92 has an annulus designed to receive a post 90 and a rim 91. The cap rotates around the post 90 and the rim 91 secures the cap 92 to the post 90.

Figure 7:
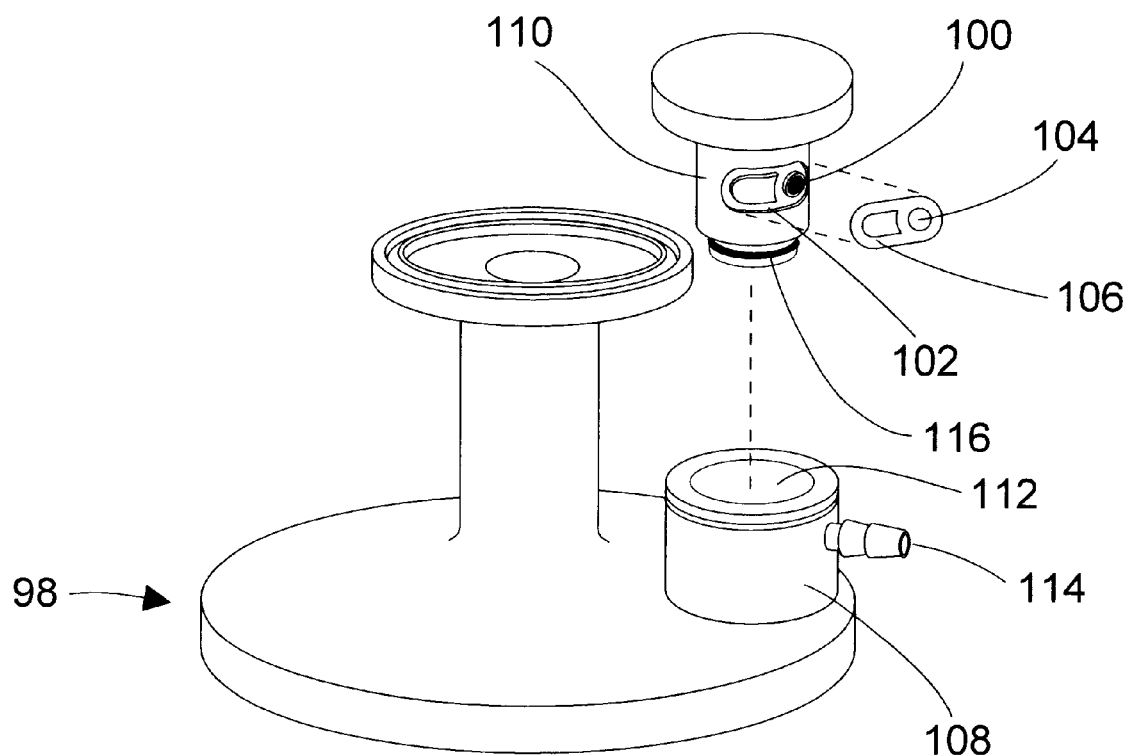
FIG. 7 shows a fourth embodiment of the seal and vent design of the present invention in an exploded view.

FIG. 7 provides a vent of the present invention wherein the exhaust port 114 remains in the same position regardless of whether the venting is on or off. Such a stationary exhaust port may have advantages for use with the venting/receptacle system described below, as the tube to the tube would not have to be flexible and could be rigidly piped.

Indeed, the embodiment of FIG. 7 provides a vent stop 110 mounted within the opening 112 of the vent 108. The stop 110 selectively opens and closes the vent 108 by rotating the stop 110 until the port 100 of the stop 110 is in fluid communication with the exhaust port 114. The port 100 is in fluid communication with the opening 112 via an internal channel (not shown. The port 100 is located within the inner seal area 104. When the vent is off, the stop 110 is rotated so the port is in communication with the sealed area defined by the closed periphery of the outer seal 106 and the outer periphery of the inner seal. The seal sits in a race 102 that prevents the seal from buckling when the stop 110 is rotated. The stop 110 is rotatably fixed to the housing 108 and seal 116 seals this rotatable fixture.

Figure 8:
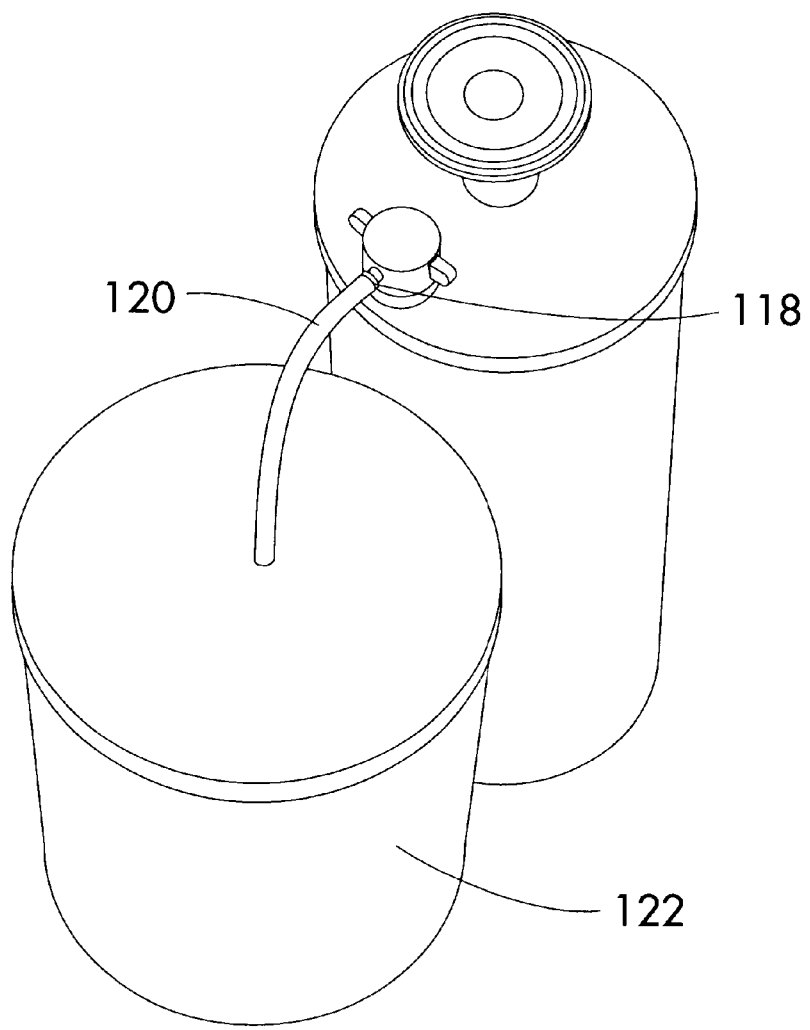
FIG. 8 shows a planar view of a venting/receptacle system that incorporates a vent of the present invention.

FIG. 8 shows a venting/receptacle system incorporating the seal and vent of the present invention to recover any fluid that may travel out the vent during the venting process. In a preferred embodiment, such a venting/receptacle system is sanitary. It is well known that some liquid will escape during venting and has been lost. The loss of this liquid is wasteful, costly (especially when filtering biopharmaceutical or photoresist products which may cost 100s of dollars per ounce) and in some instances hazardous (acids, strong bases, biologically active or contaminated fluids, etc). The present system allows for the transfer and capture of these fluids in a sterile form without outside contact. This allows for either the reintroduction of the fluid back to the system or its disposal in a safe manner.

In this embodiment, the system of either FIGS. 4, 5, 6, or 7 or modifications thereof may be used. A tube 120 to a container 122 connects the exhaust port 118. In a preferred embodiment, this container is sealed. In yet another preferred embodiment, the container 122 and tube 120 are sterile such that the external environment does not contaminate effluent entering the container.

This container 122 may be a glass or plastic bottle or a plastic, glass or metal canister having a sealed top and an opening into which the tube 120 is sealed. In this manner, a sealed pathway from the vent opening to the recovery container 122 is established and maintained. If desired, a gas vent, which is designed to prevent the introduction of outside air and or contaminants, such as a MILLEX® filter with a hydrophobic coating available from Millipore Corporation of Bedford, Mass., may be used to vent the gas recovered from the vent opening.

This system is operated by connecting one end of the sterile tube 120 to the exhaust port 118 of the vent and the other to a sterile container 122, such as a bottle sealed with a rubber plug containing one opening into which the tube 120 is sealably mounted. The vent is opened and any gas or liquid present flows through the tube 120 into the container 122. If desired, a gas vent may be provided to reduce the pressure within the container 122. In a preferred embodiment, the exhaust port 118 is fixed to the vent housing so it does not rotate during operation of the vent. In such an embodiment, it may be preferable to substitute the tube 120 with more permanent pipe or other conduit.

What is claimed is:

1. An integrated, multi-chamber sanitary seal, the seal comprising:

a plurality of walls, wherein the walls define the boundary of at least two voids through which fluid can flow and provide a sealing function, the portion of at least one wall dividing one void from at least one other void.

2. The seal of claim 1 further comprising two walls, a first outer wall forming a first outer periphery and a second wall defining a second outer periphery smaller than the first, portions of the peripheries of the first and second walls being co-exclusive such that two distinct voids within the periphery of the first outer seal are provided.

3. The seal of claim 1 further comprising two walls, a first outer wall defining a unitary circumference and a second wall positioned on an inner surface of the first wall such that a portion of the first wall and the second wall define a void having an unitary circumference smaller than that of the first unitary circumference.

4. A vent comprising a vent opening; a vent stop movably fixed to the vent opening and having a conduit with an internal and external opening; a seal receptacle area, such receptacle area defined by an annulus area and an impervious area, the annulus area in fluid communication with the internal atmosphere; and an integrated seal defining two distinct voids whose boundary walls provide sealing capability, the seal positioned on the seal receptacle such that one seal void boundary wall surrounds the annulus and one surrounds the adjacent impervious area, whereby when the vent is on, the internal opening of the vent stop is in fluid communication with the annulus and is sealed and when the vent is off, the internal opening is in fluid communication with the impervious area and is sealed.

5. A vented filter housing comprising a housing, a vent opening contained within a vent area, the opening being offset from the center of the vent area, the opening establishing a fluid pathway from the interior to the exterior of the filter, a seal having an inner seal and an outer seal, the inner seal being formed as part of the inner periphery of the outer seal, the inner seal surrounding the vent opening, the outer seal also surrounding the vent opening and surrounding the entire periphery of the vent area so as to isolate the vent area from the area outside of the vent area, a vent cap secured at its outer periphery to an outer periphery of the vent area, the cap has an opening in its bottom portion that leads by a channel to an exhaust port, the cap opening offset from the center of the bottom of the cap so as to align with the offset opening of the vent.

6. The vent of claim 4 further comprising a receptacle in fluid communication with the vent, whereby when the vent is open, the receptacle may receive effluent from the vent.

7. The vent of claim of 5 further comprising a receptacle in fluid communication with the vent, whereby when the vent is open, the receptacle may receive effluent from the vent.

8. The vent of claim of 7, wherein the receptacle is sterile, such that when the vent is closed, no pathogens may be introduced into the vent.

* * * * *